US00PP33724P2

(12) United States Plant Patent
Boekel

(10) Patent No.: US PP33,724 P2
(45) Date of Patent: Dec. 7, 2021

(54) ***CALLISTEMON* PLANT NAMED 'CALKWR'**

(50) Latin Name: ***Callistemon* hybrid**
Varietal Denomination: CALKWR

(71) Applicant: John Boekel, Koo Wee Rup (AU)

(72) Inventor: John Boekel, Koo Wee Rup (AU)

( * ) Notice: Subject to any disclaimer, the term of this patent is extended or adjusted under 35 U.S.C. 154(b) by 0 days.

(21) Appl. No.: 16/952,687

(22) Filed: Nov. 19, 2020

(51) Int. Cl.
*A01H 5/12* (2018.01)
*A01H 6/00* (2018.01)

(52) U.S. Cl.
USPC ..... Plt./226

(58) Field of Classification Search
USPC ..... Plt./226
See application file for complete search history.

(56) References Cited

FOREIGN PATENT DOCUMENTS

AU 2014117 * 11/2014

OTHER PUBLICATIONS www.ozbreed.com.au/plant-ranges/native-shrubs-groundcovers/ozbreed-red-rover-callistemon (Retrieved from the Internet on Mar. 10, 2021).*

* cited by examiner

*Primary Examiner* — Susan McCormick Ewoldt
(74) *Attorney, Agent, or Firm* — Samuel R. McCoy, Jr.

(57) ABSTRACT

A new and distinct variety of *Callistemon* plant named 'CALKWR' which is characterized by the combination of a decumbent growth habit with a flattened globular profile, an abundance of broad obovate foliage whorled around decumbent stems, prominent red juvenile foliage that matures to dark green, the absence of flowering, and the stability of all characteristics from generation to generation.

3 Drawing Sheets

Latin name of the genus and species: The Latin name of the genus and species of the novel variety disclosed herein is *Callistemon* hybrid.

Variety denomination: The inventive variety of *Callistemon* disclosed herein has been given the variety denomination 'CALKWR'.

BACKGROUND OF THE INVENTION

Parentage: The claimed plant is an openly-pollinated seedling selection which was found in cultivation at a commercial ornamental plant nursery in Koo Wee Rup, Victoria, Australia. In 2006, seed was harvested from a plurality unnamed *Callistemon citrinus* and *Callistemon* hybrid plants (none of which were patented). The seed was subsequently germinated and grown to maturity to evaluate for unique characteristics. In 2008, the inventor observed one seedling with prominent red juvenile foliage and a low, spreading growth habit. The plant was given the name, 'CALKWR'. The true parentage of the claimed plant is not known.

Asexual Reproduction: Asexual reproduction of 'CALKWR', by way of stem cuttings, was first initiated in 2008 at a commercial nursery in Koo Wee Rup, Victoria, Australia. Through greater than ten subsequent generations, the unique features of this cultivar have proven to be stable and true to type.

SUMMARY OF THE INVENTION

The cultivar 'CALKWR' has not been observed under all possible environmental conditions and the phenotype may vary somewhat with variations in environment such as temperature, day length, and light intensity, without, however, any variance in genotype. The following traits have been repeatedly observed and are determined to be the unique characteristics of 'CALKWR'. These characteristics in combination distinguish 'CALKWR' as a new and distinct *Callistemon* cultivar:

1. *Callistemon* 'CALKWR' exhibits a decumbent growth habit with a short plant height; and
2. *Callistemon* 'CALKWR' exhibits an abundance of relatively large, broad obovate foliage; and
3. *Callistemon* 'CALKWR' exhibits prominent red juvenile foliage; and
4. *Callistemon* 'CALKWR' exhibits no flowering.

BOTANICAL DESCRIPTION OF THE PLANT

Figure 1:
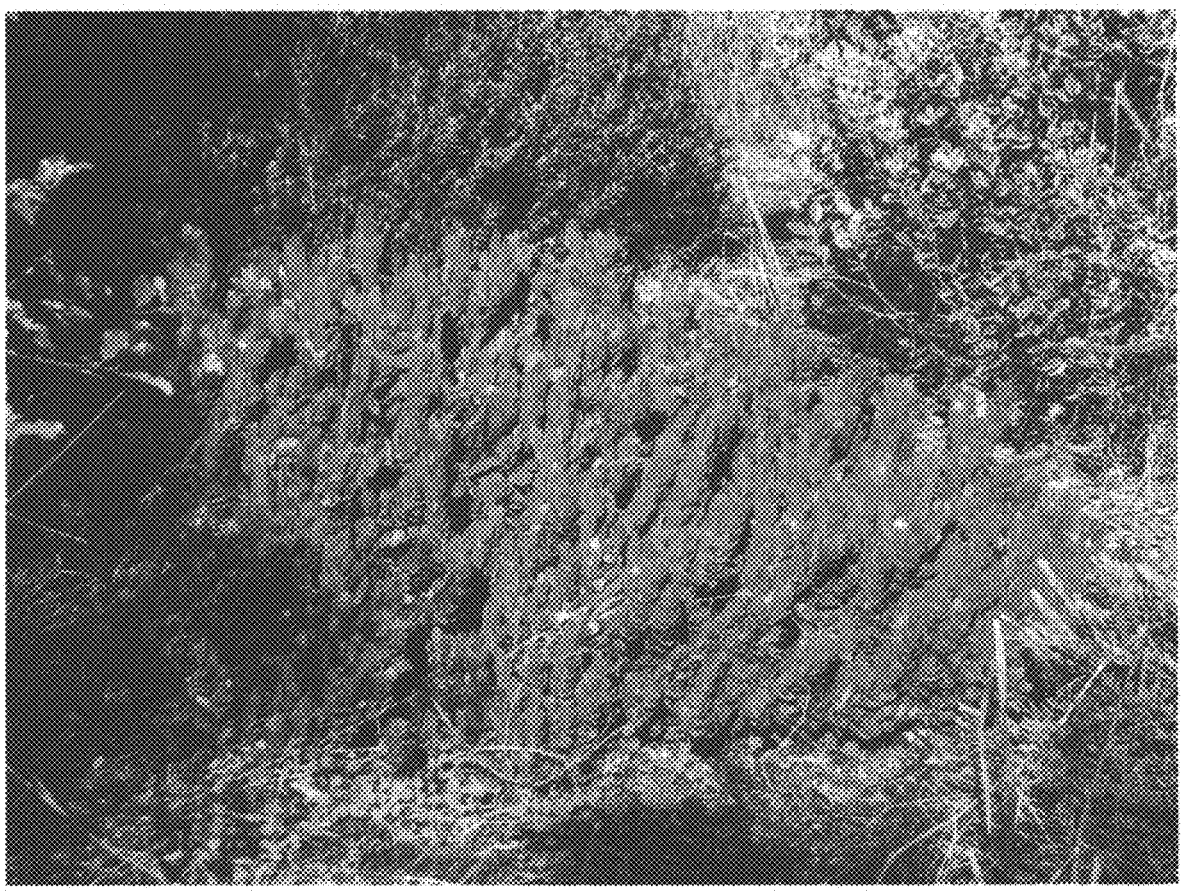
FIG. 1 illustrates, as nearly true as it is reasonably possible to make the same in color photographs of this type, an exemplary plant of 'CALKWR'. This plant is approximately 36 months old.
Figure 2:
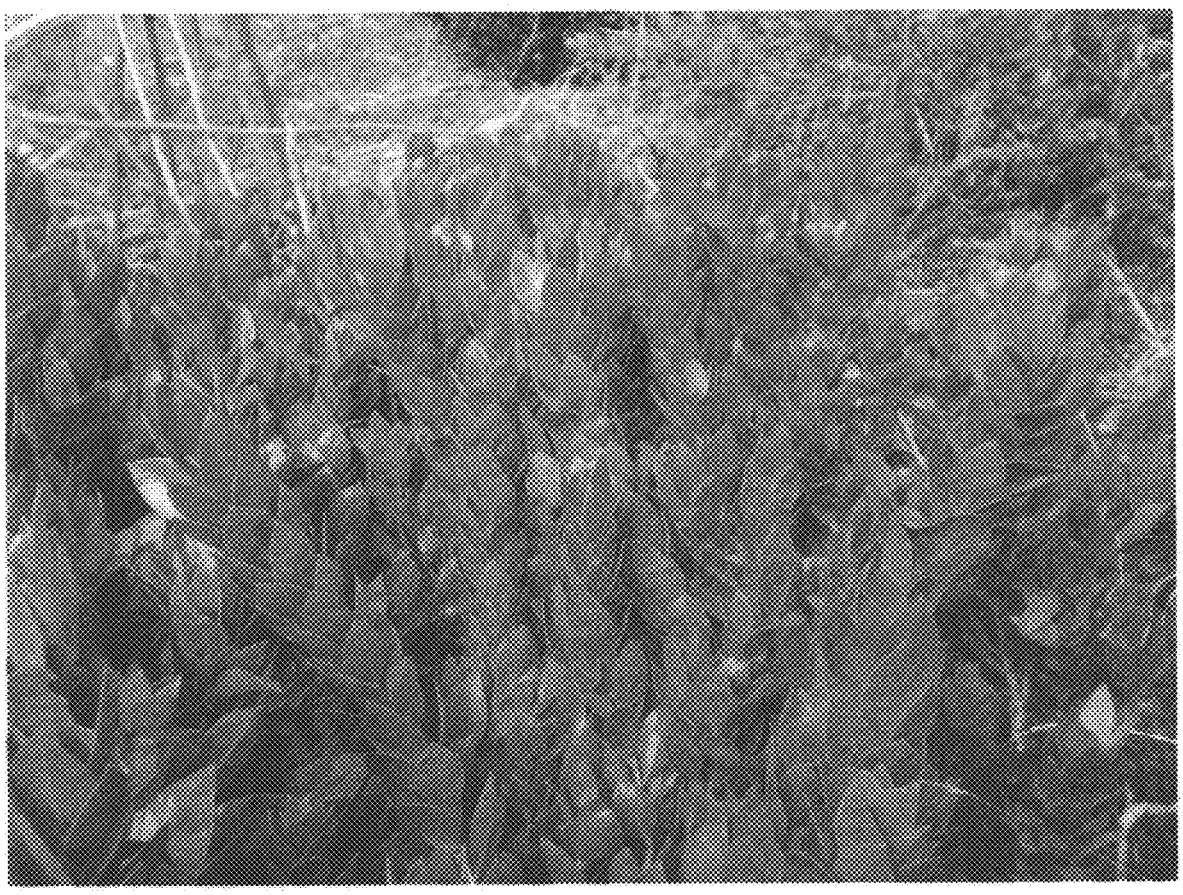
FIG. 2 illustrates, as nearly true as it is reasonably possible to make the same in color photographs of this type, the typical foliage of 'CALKWR'.
Figure 3:
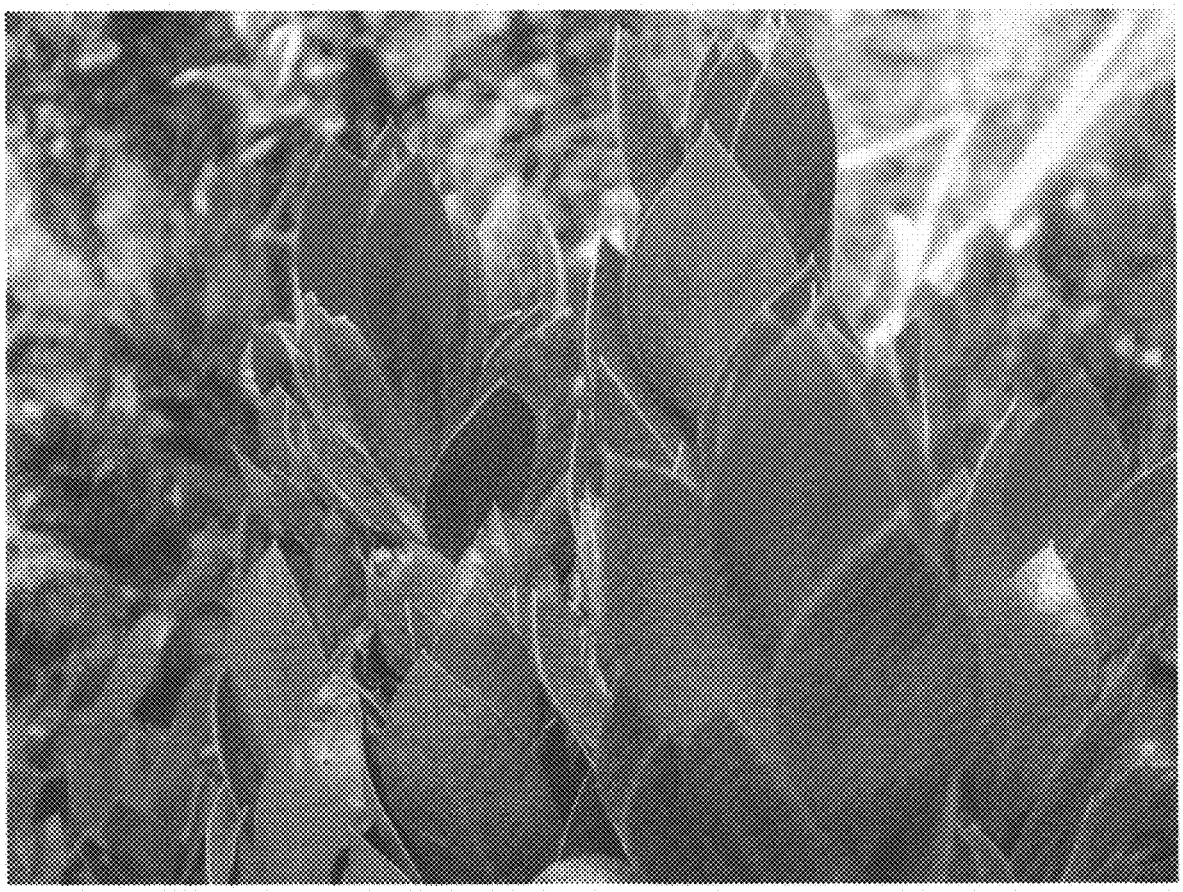
FIG. 3 illustrates, as nearly true as it is reasonably possible to make the same in color photographs of this type, the typical coloration of the juvenile foliage of 'CALKWR'.

The following observations and measurements were made in November of 2020 and describe a 36 month-old 'CALKWR' plant grown in the ground in Clarendon, New South Wales, Australia. The plant was allowed to grow with full sun exposure and maintained with regular overhead irrigation and slow-release granular fertilizer applications. No pest or disease control measures were utilized in production.

Those skilled in the art will appreciate that certain characteristics will vary with older or, conversely, with younger plants. 'CALKWR' has not been observed under all possible environmental conditions. Where dimensions, sizes, colors and other characteristics are given, it is to be understood that such characteristics are approximations or averages set forth as accurately as practicable. The phenotype of the variety may differ from the descriptions set forth herein with variations in environmental, climactic and cultural conditions. Color notations are based on *The Royal Horticultural Society Colour Chart*, The Royal Horticultural Society, London, 2015 (sixth edition).

A botanical description of 'CALKWR' and a comparison with the most similar commercial comparator known to the inventor are provided below.

Plant description:

*Growth habit*.—Semi-upright to decumbent.

*Plant profile* .—Flattened globular.

*Height*.—40 cm from the soil level to the top of the foliar plane.

*Plant spread*.—150 cm.

*Growth rate*.—Moderately fast.

*Plant vigor*.—Moderately vigorous.

*Propagation type*.—Stem cuttings.

*Time to produce a rooted cutting*.—Approximately 120 days to produce a rooted cutting at approximately 25 degrees Celsius.

*Time to produce a finished plant*.—28 weeks to produce a fully rotted 15 cm container.

*Disease resistance*.—Neither resistance nor susceptibility to typical *Callistemon* pests and diseases has been observed.

*Environmental tolerances*.—Adapt to, at least, USDA Zones 9 through 11; moderate tolerance to rain; moderate to high tolerance to wind; drought tolerant once established.

Root system:

*General*.—Moderately dense and freely branched rooting; roots are moderately fibrous.

*Distribution in the soil profile*.—Shallow to moderately deep.

Stem:

*General branching habit*.—A single main stem, freely branching from the base, with an abundance of lateral branches. Pinching isn't required but will improve branching.

*Quantity of main stems per plant*.—1.

*Abundance of lateral branches*.—Abundant.

*Length of lateral branches*.—Approximately 65 cm.

*Diameter of lateral branches*.—Approximately 0.5 cm.

*Internode length*.—Approximately 2.0 cm.

*Attitude of lateral branches*.—Decumbent to semi-upright.

*Aspect*.—Rounded.

*Texture, juvenile*.—Moderately pubescent.

*Texture, mature and oldest wood*.—Glabrous and becoming progressively fissured and furrowed with age, followed by exfoliation of the outer bark in small segments, revealing a smooth surface beneath.

*Luster*.—Slightly glossy to matte.

*Strength*.—Strong.

*Color, juvenile*.—Yellow-green, nearest to RHS 153A, and becoming progressively suffused with greyed-orange, nearest to RHS 175B, with age.

*Color, mature*.—Greyed-orange; nearest to a mixture of RHS 165B, and 175B.

Foliage:

*Arrangement*.—Whorled.

*Division*.—Simple.

*Attachment*.—Petiolate.

*Foliage abundance*.—Very abundant; approximately 12 to 15 leaves per 10 cm of lateral branch.

*Attitude*.—Upward and outward.

*Lamina*.—Shape — Broad obovate. Aspect — Flat to slightly carinate. Dimensions — 6.5 cm long and 2.3 cm wide. Apex — Apiculate. Base — Attenuate. Margin — Entire, ciliate; not undulated. Texture of the juvenile foliage, adaxial surface — Densely pubescent. Texture of the juvenile foliage, abaxial surface — Densely pubescent. Texture of the mature foliage, adaxial surface — Coriaceous; glabrous. Texture of the mature foliage, abaxial surface — Coriaceous; glabrous. Luster of the juvenile foliage — Matte to slightly glossy. Texture of the mature foliage, abaxial surface — Moderately glossy. Color — Juvenile foliage, adaxial surface — Greyed-purple, nearest to RHS N186C. Juvenile foliage, abaxial surface — Greyed-purple, nearest to RHS 186C. Mature foliage, adaxial surface — Green, nearest to RHS NN137A. Mature foliage, abaxial surface — Yellow-green, nearest to RHS 147A. Venation — Pattern — Pinnate. Color, adaxial surface — Same as the surrounding foliage; green, nearest to RHS NN137A. Color, adaxial surface — Same as the surrounding foliage; yellow-green, nearest to RHS 147A.

*Petiole*.—Length — 0.25 cm. Diameter — 0.2 cm. Strength — Strong. Texture, juvenile — Pubescent. Texture, mature — Smooth; glabrous. Luster — Slightly glossy. Color, adaxial and abaxial surfaces — Juvenile petioles are colored yellow-green, nearest to RHS 153D, and lightly suffused with greyed-orange, nearest to RHS 175B. Mature petioles are colored yellow-green, nearest to RHS 147A.

Inflorescence: To date, no flowering has been observed on the mother plant or any progeny therefrom.

Flower bud: To date, no flowering has been observed on the mother plant or any progeny therefrom.

Flower: To date, no flowering has been observed on the mother plant or any progeny therefrom.

Reproductive organs: To date, no flowering has been observed on the mother plant or any progeny therefrom.

Fruit and seed: To date, no fruiting has been observed on the mother plant or any progeny therefrom.

Comparison With the Parent Plants

The true parentage of the claimed plant is unknown and therefore no comparisons are available.

Comparison With the Closest Known Comparator

Plants of the new cultivar 'CALKWR' differs from the most similar commercial cultivar known to the inventor, *Callistemon* 'Endeavour' (not patented), in the following characteristics described in Table 1 below.

TABLE 1

| Characteristic | 'CALKWR' | 'Endeavour' |
|---|---|---|
| Growth habit. | Spreading and somewhat decumbent. | Upright. |
| Plant size. | Shorter and generally smaller than 'Endeavour'. | Taller and generally larger than 'CALKWR'. |
| Foliage shape. | Broad obovate. | Lanceolate. |
| Flowering habit. | Non-flowering. | Floriferous. |

That which is claimed is:

1. A new and distinct variety of *Callistemon* plant named 'CALKWR', substantially as described and illustrated herein.

* * * * *